United States Patent [19]
Dahl et al.

[11] 4,146,791
[45] Mar. 27, 1979

[54] METHOD AND MEASURING DEVICE FOR TESTING THE SUPPORT AND OR COVERING OF AN OIL OR GAS PIPELINE

[75] Inventors: John B. Dahl, Skedsmokorset; Johnny Schatvet, Festund; Kristian Skarsvag, Li, all of Norway

[73] Assignee: Institutt for Atomenergi, Kjeller, Norway

[21] Appl. No.: 798,379

[22] Filed: May 19, 1977

[30] Foreign Application Priority Data

May 20, 1976 [NO] Norway ................................ 761710
Sep. 14, 1976 [NO] Norway ................................ 763137

[51] Int. Cl.² .......................... G01N 23/00; G01V 5/00
[52] U.S. Cl. ................................ 250/358 P; 250/253
[58] Field of Search .................. 250/253, 358 D, 359, 250/360, 303

[56] References Cited
U.S. PATENT DOCUMENTS 3,064,127  11/1962  Green et al. .................. 250/358 P Primary Examiner—Alfred E. Smith
Assistant Examiner—Janice A. Howell
Attorney, Agent, or Firm—Watson, Cole, Grindle & Watson

[57] ABSTRACT

A measuring device to be conveyed through an oil or gas pipeline at the bottom of the sea is provided for measuring the radioactivity of the surroundings along the pipeline. Thus, the support and/or the covering of the pipeline may be tested, the sea bottom sediments having an appreciably higher gamma radiation source strength than the sea water and the oil or gas which flow through the pipeline.

19 Claims, 11 Drawing Figures

METHOD AND MEASURING DEVICE FOR TESTING THE SUPPORT AND OR COVERING OF AN OIL OR GAS PIPELINE

The present invention relates to the testing of the position of an oil or gas pipeline at the ocean floor.

An oil or gas pipeline at the ocean floor, deep within the sea, typically buried in sand with a good base support in order to avoid, among other things, excessive strains on the pipeline under the influence of external loads. In locations where such burying of the pipeline is difficult, e.g. due to a rocky bottom, the best support and protection possible is secured by means of levelling the bottom and covering the line by prefabricated concrete protectors. Because of movements in the sea, the sand around the pipeline may be washed away and the pipeline laid bare. This may result in the following inconveniences:

(a) Great strains on the pipeline portions which are exposed to the water;
(b) Possibilities that bottom trawl and ship anchors may be hooked up in the pipeline:
(c) Possibilities that shipwrecks may damage the pipeline.

It has always been difficult to ascertain that a pipeline is adequately covered and supported, and the surveillance problems increase with increasing water depths. Up to now such surveying has been performed by divers or by means of underwater photographing. It is, however, not always possible to achieve a satisfactory check by means of visual means, and at any rate it may hardly be possible in practice to survey the whole length of an extended pipeline in this way. Thus, the present invention relates to an improved method for testing the support and/or covering of an oil or gas pipeline situated at the bottom of a water formation, particularly at the ocean floor, and according to the invention this method is characterized in that the natural radioactivity of the materials surrounding said pipeline is measured and compared with previously measured values of natural radioactivity of water and the supporting and/or covering materials, respectively.

This method is of particular interest when pipelines buried in sand are to be surveyed.

The method according to the invention takes advantage of the fact that the sea bottom normally has a natural radioactivity due to potassium—40, uranium and thorium with their daughter products. In comparison with this radioactivity, the radioactivity of sea water, oil and natural gas is very meagre.

By use of the method according to the present invention the natural radioactivity of the surroundings may be gauged by means of a measuring device which is conveyed through the pipeline and comprises at least one radiation detector.

The counting rate of such detectors is a measure of the radioactivity of the volume viewed by the detectors, and when the counting rate is integrated over small time intervals, it may form a counting profile as a function of measured distance along the pipeline. Such a profile may be established as soon as the pipeline has been put into operation, and similar measurements at a later date may reveal if the profile has been changed. Each change of the profile may be ascribed to a change of the support and/or covering of the pipeline.

According to a feature of the present invention the measuring device is conveyed through the pipeline by the oil or gas flow through the line.

According to another feature of the invention the measuring device is adapted to record the values measured by the radiation detector.

According to a further feature the measuring device records the counts produced by a joint counter disposed to count every pipe joint passed by the device, in order to gauge the distance passed along the pipeline.

In order to collect the measured values recorded in the measuring device, according to a feature of the invention, said device is removed from the pipeline after its passage through the same and the recorded values registered before further use of the measuring device.

The measuring device according to the invention is characterized in that it comprises at least one instrument casing detachably connected with a casing carrier.

The measuring device may be provided with a drive sleeve. The casing carrier of the device may be provided with wheels disposed to run along the inside of the pipeline wall. According to the invention such wheels may be disposed peripherally around the measuring device in a manner to effect a centering of the device in the pipeline.

Furthermore the wheels may be connected with the casing carrier by means of spring biased arms disposed to urge the wheels against the pipeline wall.

According to a feature of the invention the instrument casing may be provided with a radiation detector disposed to feed an electronic memory for storing measured values. According to a further feature the radiation detector is a plastic detector or alternatively a NaI (Tl) crystal.

In a preferred embodiment of the measuring device according to the invention at least one set of four radiation detectors having approximately the same counting efficiency is symmetrically disposed with respect to the axis of the pipeline, the counts of each radiation detector being compared with the counts of the other detectors in the set.

With this embodiment it will not be necessary to establish a counting profile as a function of measured distance along the pipeline, as indicated above. By taking advantage of the symmetrical disposition of the radiation detectors with respect to the axis of the pipeline, when comparing the respective counts of the detectors, it is possible directly to test the support and/or the covering of the pipeline, even when measured reference values for an adequately covered line are missing.

The invention will now be further illustrated with reference to the accompanying drawings on which:

Figure 1:
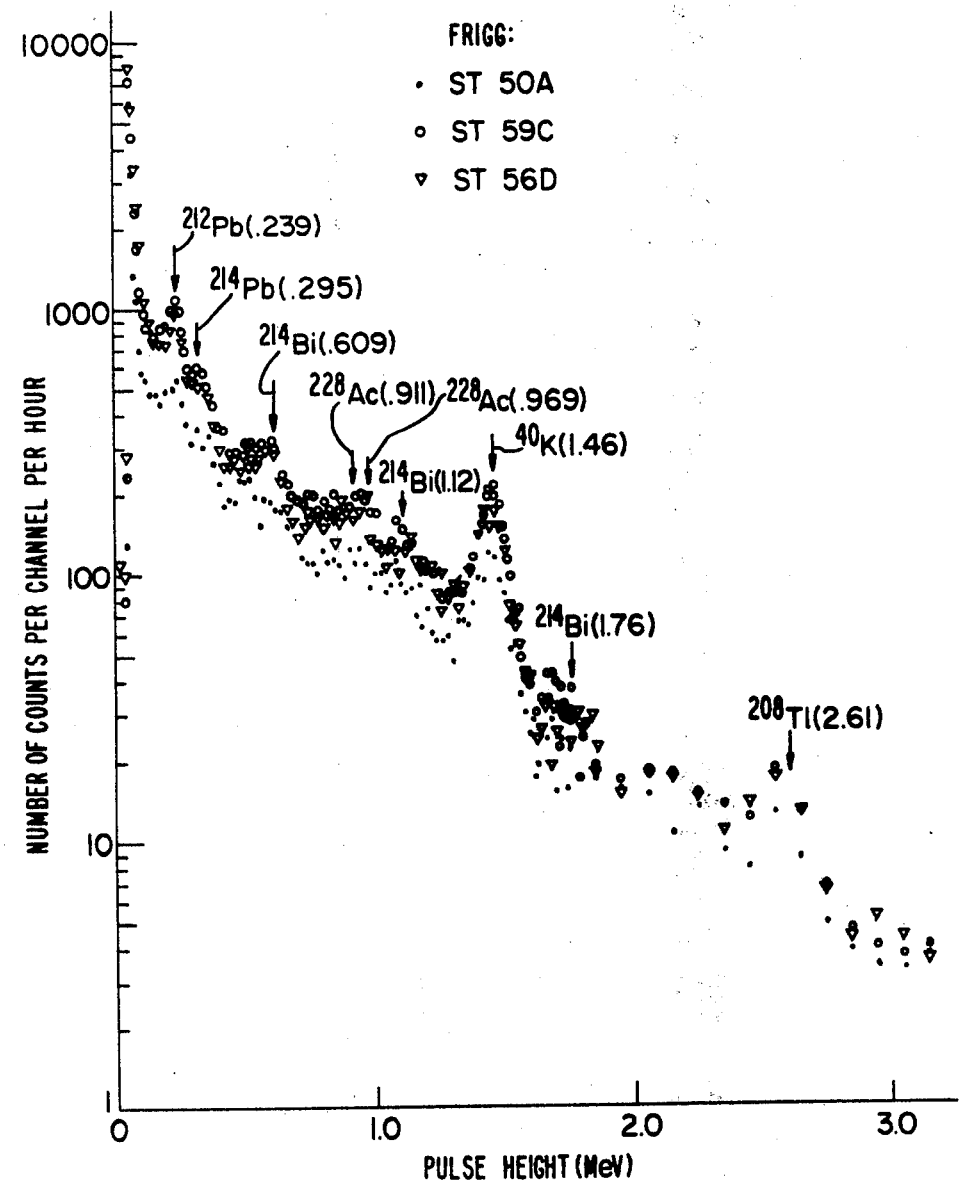
FIG. 1 is a graph showing the pulse height distribution measured with a standard geometry factor on sediment samples from the Frigg oil field in the North Sea.

FIG. 1 indicates the number of pulses per channel per hour as a function of pulse height (the pulse height distribution) for sediment samples from the Frigg oil field in the North Sea, measured by means of a gamma ray spectrometer with a NaI(Tl) crystal (Thallium activated NaI crystal) as a detector. This gamma ray spectrometer sorts the received pulses according to their pulse height, which is a function of the gamma ray energy. The indicated symbols ST50A, ST59C and ST56D refer to different sediment samples, as indicated in table V. The detected radioactivity is due to potassium—40, uranium and thorium with their daughter products. Some of the isotopes involved and the corresponding gamma ray energies are indicated in the Figure by means of arrows.

The method according to the invention has been investigated by means of mathematical models in order to find out if statistically significant results are obtainable under typical conditions for a certain length of a pipeline.

Two simple models have been developed, i.e. one model for an infinite block with screen for the purpose of calculating the intensity of gamma radiation just above the ocean floor, and a cylindrical model for the purpose of calculating the intensity inside an instrument casing disposed in a pipeline.

In the first case (infinite block with screen) the integrated intensity J may be expressed by the following formula:

$$J = \tfrac{1}{2} S_{vo} \int_{\theta=0}^{\tfrac{1}{2}\pi} \int_{\rho=X_2}^{\infty} tg\,\theta\, B\, e^{-B n}\, d\rho\, d\theta,$$

and in the other case (within an instrument casing in a pipeline) by the subsequent formula:

$$J = (1/\pi) \sum_{m=1}^{2} \left[ S_{v1} \int_{\phi=0}^{\tfrac{1}{2}\pi} \int_{\theta=0}^{\tfrac{1}{2}\pi} \int_{\rho=X_{a,m}}^{X_{c,m}} B_{1,m} e^{-B n l, m}\, d\rho\, d\theta\, d\phi + S_{vo} \int_{\phi=0}^{\tfrac{1}{2}\pi} \int_{\theta=0}^{\tfrac{1}{2}\pi} \int_{\rho=X_{c,m}}^{\infty} B_{o,m} e^{-B no, m}\, d\rho\, d\theta\, d\phi \right]$$

Here the symbols have the following meaning:

J—radiation intensity, gamma rays per $cm^2$ per sec.
$S_{vi}$—source strength, gamma rays per $cm^3$ per sec.
$B_n, B_{ni,m}$—number of free path lengths
$B, B_{o,n}$—assembly factor
$X_2, X_{a,m}, X_{c,m}$—integration limits, cm
$\rho$—coordinate, cm
$\theta$—polar angle
$\phi$—azimutal angle The mathematical model of a cylinder was tested by means of measurements performed with a gamma ray spectrometer having a detector (NaI(Tl)crystal, diameter 2.5 cm and length 5.1 cm) axially located in a pipe. Two pipe embodiments were used, i.e. one horizontal pipe with diameter 19.5 cm and length 220 cm, and another pipe with dimaeter 4.8 cm and driven vertically into the bottom ground. The results of these measurements are given in Table I.

Table I

Measurements made at Fetsund

| Experiment | Layer thickness (cm) | | | | | Integrated counting rate (min$^{-1}$) | |
|---|---|---|---|---|---|---|---|
| | Sediment | Water | Concrete | Steel | Water in cylinder | Measured | Corrected for background |
| 1 | 117[a] | 58[b] | 0 | 0,4 | 0 | 2297 | 2191 |

Table I-continued

Measurements made at Fetsund

| Experiment | Layer thickness (cm) | | | | | Integrated counting rate (min$^{-1}$) | |
|---|---|---|---|---|---|---|---|
| | Sediment | Water | Concrete | Steel | Water in cylinder | Measured | Corrected for background |
| 2 | 0 | 250[c] | 5,0 | 3,4 | 3,8 | 414 | 308 |
| 3 | 0 | 250[c] | 0 | 3,4 | 3,8 | 106 | |
| 4 | 60[a] | 53[b] | 5,0 | 3,4 | 3,8 | 740 | 634 |
| 5 | 0 | 250[c] | 5,0 | 1,1 | 6,1 | 813 | 707 |

[a]Above the detector
[b]Water depth
[c]Above and below the detector.

The experiments 1 and 4 were made in the river Glomma at Fetsund (Norway), and the experiments 2,3 and 5 were performed from the ice on a small lake near by.

The achieved results were subjected to the following considerations:

(1) Comparison of certain counting rate ratios, as observed and calculated, respectively; see Table II.
(2) Comparison of absolute source strengths as calculated by means of the cylindrical model (from data in Table I), with source strengths measured on samples by means of a gamma ray spectrometer with standard geometry factor and a 7.6 cm × 7.6 cm NaI(Tl) crystal as detector, see Table III.

Table II

| Ratio | Relative counting rates | |
|---|---|---|
| | Experimental | Calculated |
| $K_0$ | 2,05 | 1,70[a] |
| $K_1$ | 2,29 | 1,93 |
| $K_2$ | 0,29 | 0,34[a] |

[a]Calculated for a ratio $S_{vo}/S_{v1} = 0.44$, where $S_{vo}$ and $S_{v1}$ are source strength (gamma rays/$cm^3$ · sec) in sediment and concrete respectively.

The designations are as follows:
$K_o = (J_o + J_1)^{(4)}/J_o^{(2)}$,
$K_1 = J_1^{(5)}/J_1^{(2)}$, and
$K_2 = (J_o + J_1)^{(4)}/J_o^{(1)}$, where $J_i$ stands for the intensity of gamma radiation (gamma rays/$cm^2$·sec), the upper index refers to the experiment number (see Table 1), and the lower indices $i = 0,1$ refer to radiation from sediment and concrete, respectively.

Table III

Source strengths of sediment and concrete

| Source | In situ[a] $S_v$(gamma rays/($cm^3$ . s)) | $S_w$(nCi/kg) | Standard geometry $S_w$(nCi/kg) |
|---|---|---|---|
| Sediment | 0,73[b] | 10,1 | 9,2[a] |
| Sediment | 0,77[c] | 10,6 | |
| Concrete | 1,14[d] | 10,4 | 13,7 |
| Concrete | 1,36[e] | 12,4 | |

[a]The density of the sediment was measured to 1.95 g/$cm^3$ with a water content of 20% by weight.
[b]From experiment 1.
[c]From experiment 4 (together with 2)
[d]From experiment 2.
[e]From experiment 5.

As illustrated in Tables II and III, good agreements are achieved in both cases.

Similar measurements just above the sea bottom were in good agreement with the model of an infinite block.

Source strengths in the North Sea were calculated by two methods:

(1) From measurements performed on the sea bottom offshore Yorkshire in England (J. M. Miller and G. D. Symons, Nature 242 (1973) 184 by means of the model for an infinite block, see Table IV.

(2) From samples of sediments from the North Sea, concrete, oil and off-scrapings from oil as measured with standard geometry factor, see Table V.

Table IV

Source strengths of the sea bottom offshore the Yorkshire coast.

| Description | Counts $(s^{-1})$[a] | $S_v$(gamma rays/ $(cm^3 \cdot s))$ | $S_w$(nCi/kg) |
|---|---|---|---|
| Marine limestone | 30 | 0,39 | 5,3 |
| Marine clay slate with band of limestone | 90 | 1,2 | 16 |
| Marine clay slate | 180 | 2,3 | 32 |

[a] Measured with a 7.6 × 7.6 NaI(Tl) detector with a bias of 50 keV.

Table V

Source strengths of samples measured with standard geometry.

| Sample | $S_w$(nCi/kg) | $S_v$(gamma rays/$(cm^3 \cdot s))$ |
|---|---|---|
| Sediment from: | | |
| Frigg | 4,9 | 0,29 |
| Beryl | 3,9 | 0,23 |
| Alwyn | 3,5 | 0,20 |
| Frigg (ST50A) | 7,7 | 0,45 |
| Frigg (ST56D) | 19,8 | 1,17 |
| Frigg (ST59C) | 19,5 | 1,15 |
| Oil | 0 | |
| Oil off-scrapings | 1,3 | 0,04 |
| Concrete | 4,2 | 0,38 | it is observed that the respective values of the source strengths of the oil field sediments, as found by the above methods 1) and 2), respectively, are mainly within the same order of magnitude. The radioactivity is not measureable for oil and very small for oil off-scrapings.

The natural gamma radiation may be detected by means of detectors of various types, but according to the invention a NaI(Tl) crystal or a plastic scintillator is preferred for this purpose. The former has higher efficiency, but with large detectors the difference is relatively small. Furthermore, the Nai(Tl) crystal produces about three times more light than the plastic scintillator for the same amount of energy. On the other hand the plastic scintillator is more rugged and less expensive than the NaI(Tl) crystal.

By means of the cylindric model the number of counts as a function of time is calculated for a standard 34 Inch (about 86 cm) oil pipeline, with typical source strengths as indicated in Tables IV and V, and with:

(1) a NaI(Tl) crystal (7.6 × 7.6 cm) in axial position, (2) a plastic scintillator (diameter 15.2 cm and length 30.5 cm) in axial position, (3) four plastic scintillators of the same size as indicated above at a distance of 27 cm from the axis and with angles of 90° between the respective detectors.

The bias applied is 50 keV with alternative 1) and has with alternatives 2) and 3) a value corresponding to 70% of the counting rate with 50keV. Calculations show that a factor of 5 may be gained as to the counting rate by switching from alternative 1) to alternative 2). Further a counting rate factor of 1.5 is gained by displacing a detector from the axial position to said position 27 cm away from the axis, and a factor of 4 is gained by using four detectors instead of a single one.

Thus the counting rate is 30 times higher with alternative 3) than with alternative 1).

The calculations have been performed for one single value ($S_v = 0.39$ gamma rays per $cm^3$ per sec.) of source strength in concrete, and for two values of source strength in sediment ($S_v = 0.39$ and 1.2 gamma rays per $cm^3$ per sec.) Four different conditions have been assumed:

(1) Oil pipeline with concrete jacket buried in the sea bottom, (2) Oil pipeline with concrete jacket freely suspended in water, (3) Oil pipeline without concrete jacket buried in the sea bottom, (4) Oil pipeline without concrete jacket freely suspended in water, which is supposed to give the appropriate radiation background from detector and instrument casing (see C. G. Clayton, Proc. Panel of Nuclear Techniques in Geochemistry and Geophysics, Vienna, 1974 (IAEA, Vienna, 1974) 109).

In all cases a wall thickness of 1.4 cm and an internal diameter of 20 cm have been assumed for the instrument casing.

It may be assumed that significant results are obtainable for a certain line length, which in the present case is set to 6 m. With a speed of 3 m/sec for the casing carrier, this length corresponds to 2 seconds. The results obtained are indicated in the FIGS. 2–4.

Figure 2:
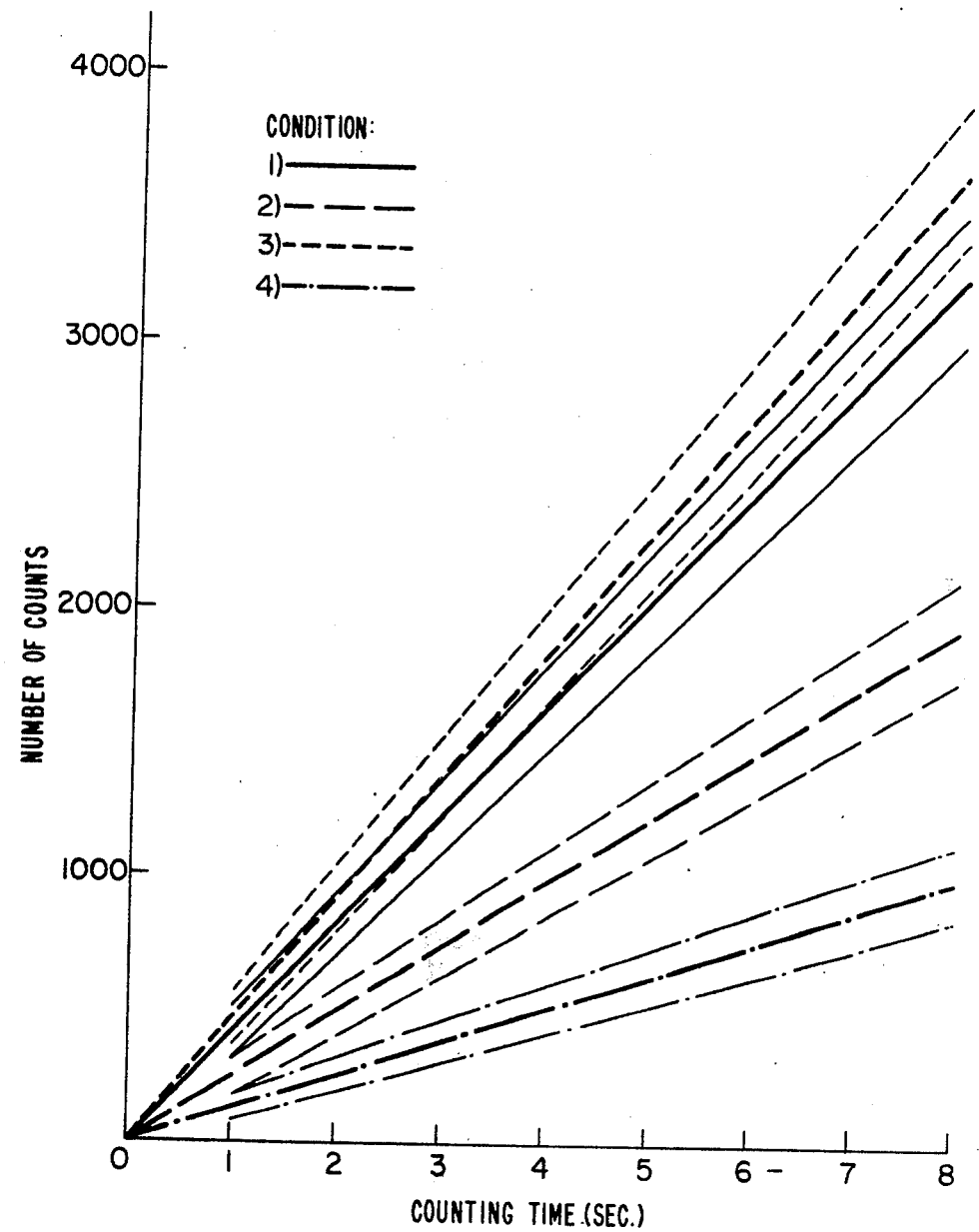
FIGS. 2, 3 and 4 are graphs showing the number of counts made by the radiation detector as a function of the counting time under various conditions.
Figure 3:
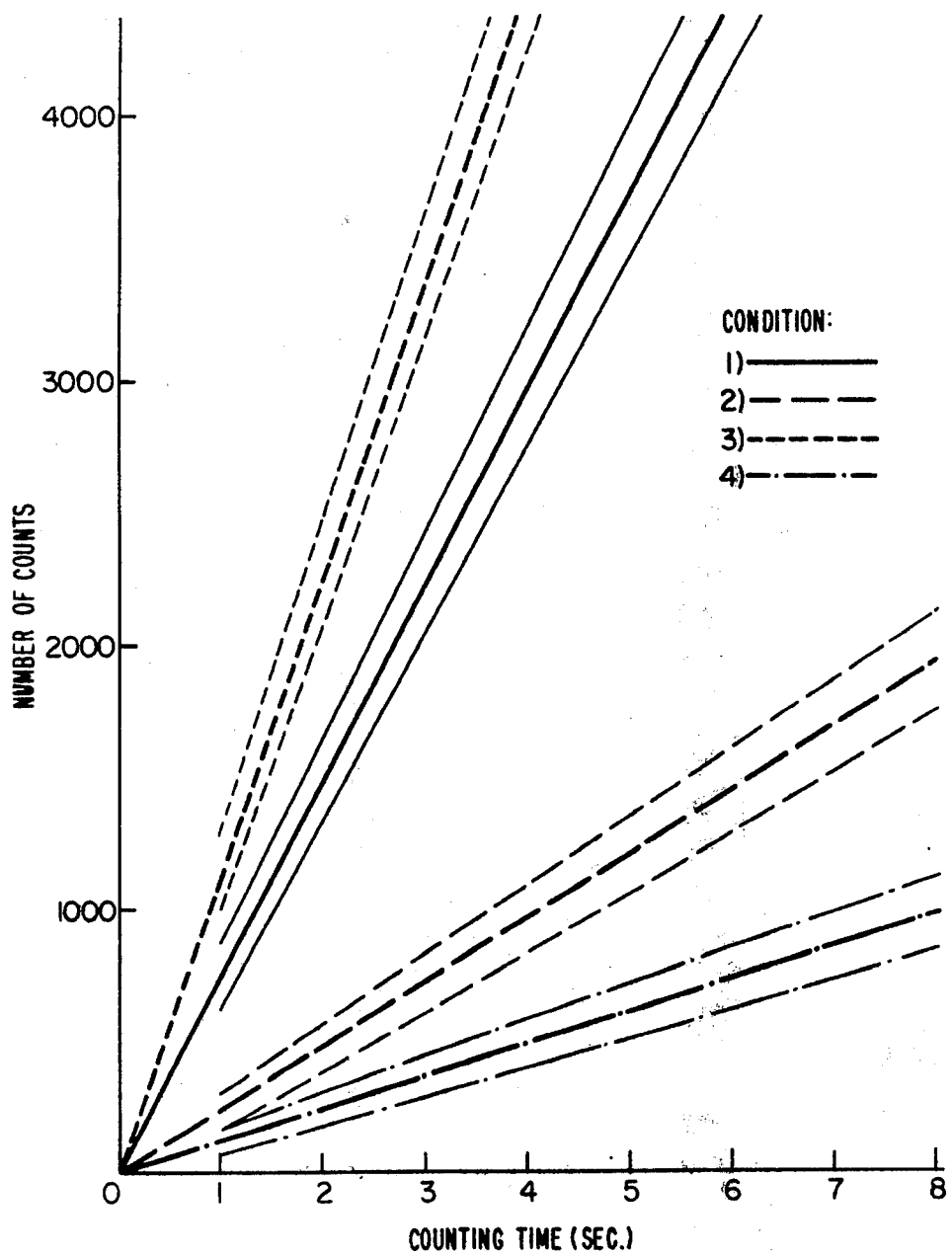
Figure 4:
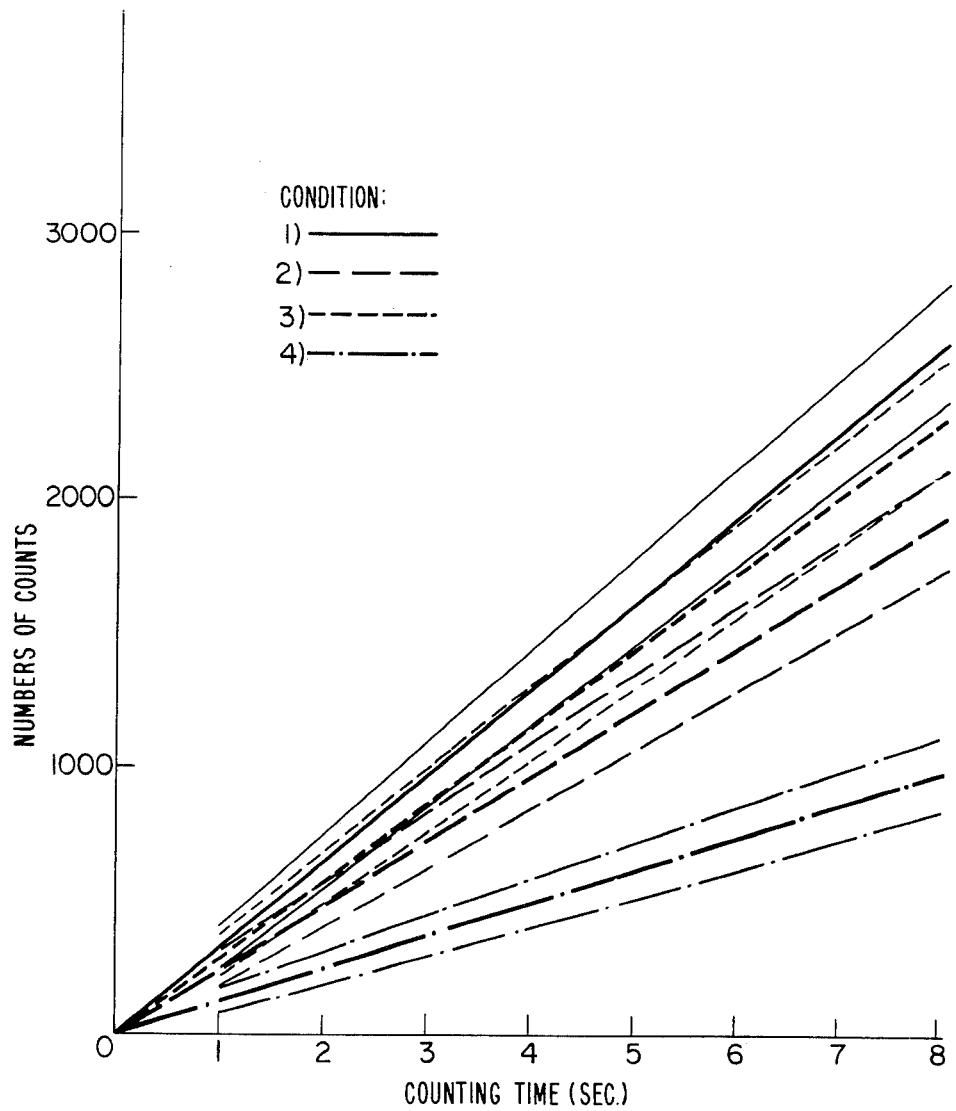

These FIGS. 2–4 show the number of counts as a function of counting time, as measured by means of four radiation detectors in the form of plastic scintillators (diameter 15.2 cm, length 30.5 cm) which are offset 27 cm from the axis of an oil pipeline (see FIG. 5), for the four assumed conditions.

The thinner lines on each side of each of the thicker main graphs represent the sum of three standard deviations. Here, systematical errors are assumed to give the same condition as statistical errors.

The assumed source strengths of the sediment is 0.39, 1.2 and 0.20 gamma rays per $cm^3$ per sec, respectively, in the FIGS. 2, 3 and 4. The source strength of concrete is in all Figures assumed to be $S_v = 0.39$ gamma rays per $cm^3$ per sec.

As a conclusion of the results obtained, it may be stated that a 7.6 × 7.6 cm NaI(Tl) crystal in axial position (alternative 1) is not able to differentiate between the four conditions indicated above, whereas an axially disposed plastic scintillator with diameter 15.2 cm and length 30.5 cm may be able to distinguish between said four conditions with high source strengths, and four such detectors offset 27 cm from the axis are able to differentiate between the four conditions with the most usual source strengths, but not with very low source strengths, see FIG. 4.

It may thus be concluded that a detector system e.g. consisting of four plastic scintillators, is able to distinguish between certain well defined conditions concerning the support and/or covering of oil pipelines with typical source strengths of the surrounding material, in the course of a time interval as short as 2 seconds.

In a gas pipeline the absorption of gamma radiation will be less than in an oil line, and thus the counting rate for a given detector correspondingly higher.

Figure 5:
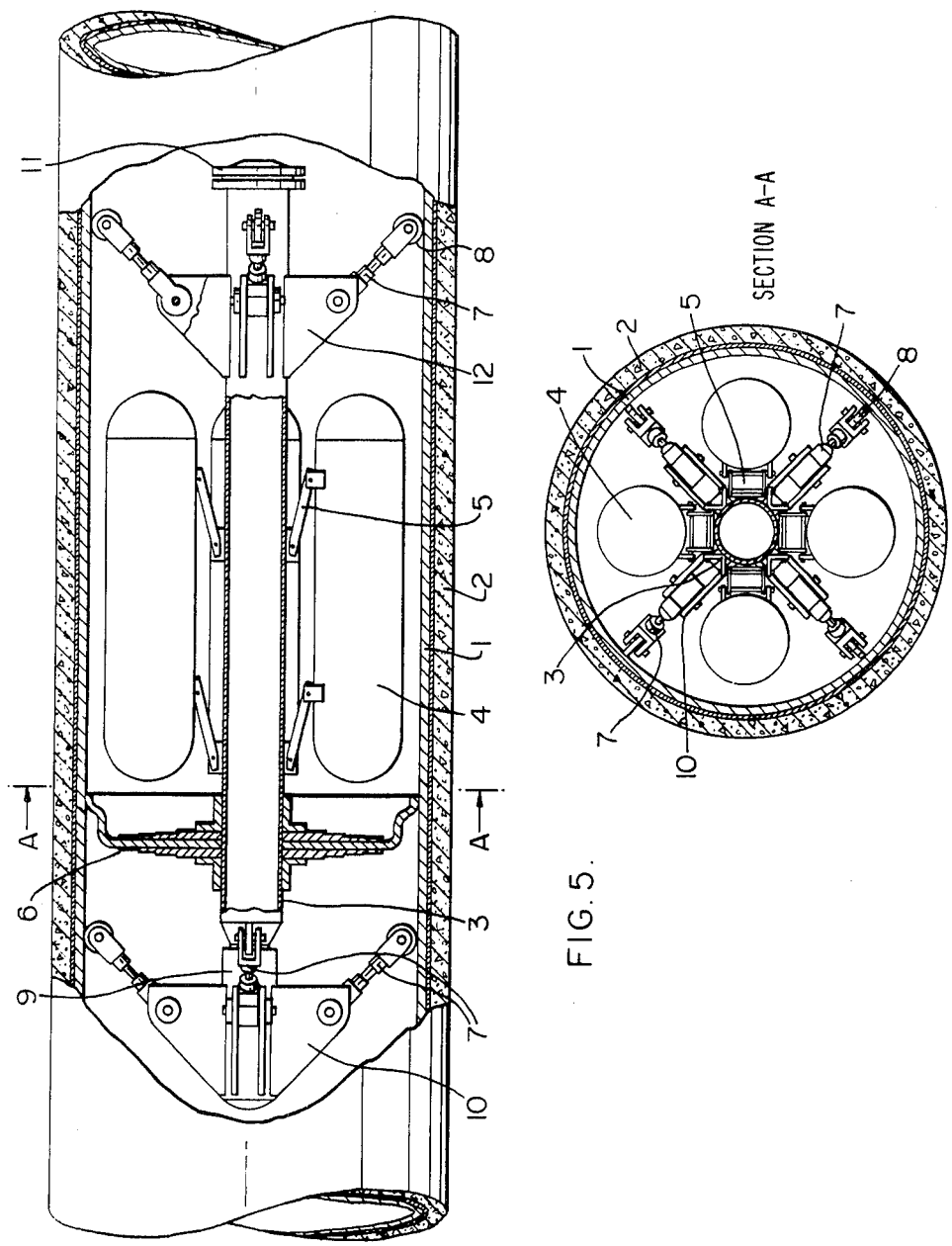
FIG. 5 shows a possible embodiment of the measuring device according to the invention.

An exemplified embodiment of the measuring device according to the invention is shown in FIG. 5.

In this Figure a pipeline 1 is surrounded by a concrete jacket 2. Within this pipeline a measuring device is movably disposed, comprising a casing carrier 3 with four identical instrument casings 4. The instrument casings are detachably fixed to the carrier by means of spring biased hinges 5. The measuring device is propelled by the oil flow by means of a drive sleeve 6. In order to secure a centering of the device in the pipeline it is provided with eight spring biased control arms 7 having wheels 8 disposed to run along the inside of the pipeline wall. When the measuring device is to pass a bend on the line, bias springs (not shown) on the control arms 7 and the hinges 5 will be compressed, thus preventing the device from being stuck in the pipeline. The control arms are fixed to brackets 10, 12 which in turn are connected with the head 9 or the rear part of the casing carrier. The carrier is provided with a detachable cover 11.

The measuring device is inserted in the pipeline through a shunt line, which initially is free from oil. After closing the inlet to the shunt line it may be opened to the main pipeline in order that the measuring device may be guided into the same.

The weight of the measuring device should be kept as low as possible in order to minimise the wear on the wheel. As to the structural design, the most important feature is to prevent the device from getting stuck in the pipeline, as this may have the most serious consequences for the operation of the line. If, however, the measuring device nevertheless should get stuck in the line, the various components of the same may be torn away and carried with the oil or gas flow out of the pipeline.

The instrument casing is designed to endure statical pressures up to 150 kp/cm². This casing may be readily removed from the carrier and the recorded data may be extracted without opening the casing.

The joint counter is disposed to register every pipe joint along the line, either mechanically or by supersonic means.

The instrument casing contains the following components:
- a detector for gamma radiation, which may be a NaI(Tl) crystal or a plastic scintillator adapted to emit a light pulse for each scattered or absorbed gamma ray,
- a photomultiplier which produces an electric pulse for each received light pulse,
- a combined amplifier and pulse shaper, which amplifies and suitably shapes said electric pulse,
- a discriminator adapted to produce a standard electric output for each input pulse exceeding a certain bias value,
- memory means adapted to store relevant operational data (e.g. number of output pulses from the discriminator during a counting period and the reference number of that period),
- a chargeable battery with power supply,
- terminal plugs for extracting recorded data from the casing.

Normally, the instrument casing will only be opened for periodical maintenance work.

Alternatively, parts of the electronic equipment may be located in the casing carrier. These parts may then be inserted in the carrier through the opening covered by the cover 11, and in this case the instrument casings must be electrically connected with the carrier by means of cables (not shown in FIG. 5). However, at least said radiation detectors and photomultipliers should be disposed in the instrument casings.

In the preferred embodiment of the measuring device according to the invention at least one set of four peripherally disposed radiation detectors is symmetrically arranged with respect to the horizontal and vertical planes, respectively, through the axis of the device.

With this embodiment the measuring device is preferably installed in the pipeline in such a manner that the axis of the device is coincident with the pipeline axis.

The measuring device is preferably shaped to be approximately symmetrical with respect to the horizontal and vertical planes, respectively, through the axis of the device. Further, a stabilising load arrangement may be suspended below the centre of gravity of the device. This load arrangement should be disposed not to screen the active radiation detectors of the device, but may otherwise be designed in any suitable way for the purpose of preventing a revolving of the device in the pipeline.

Figure 6:
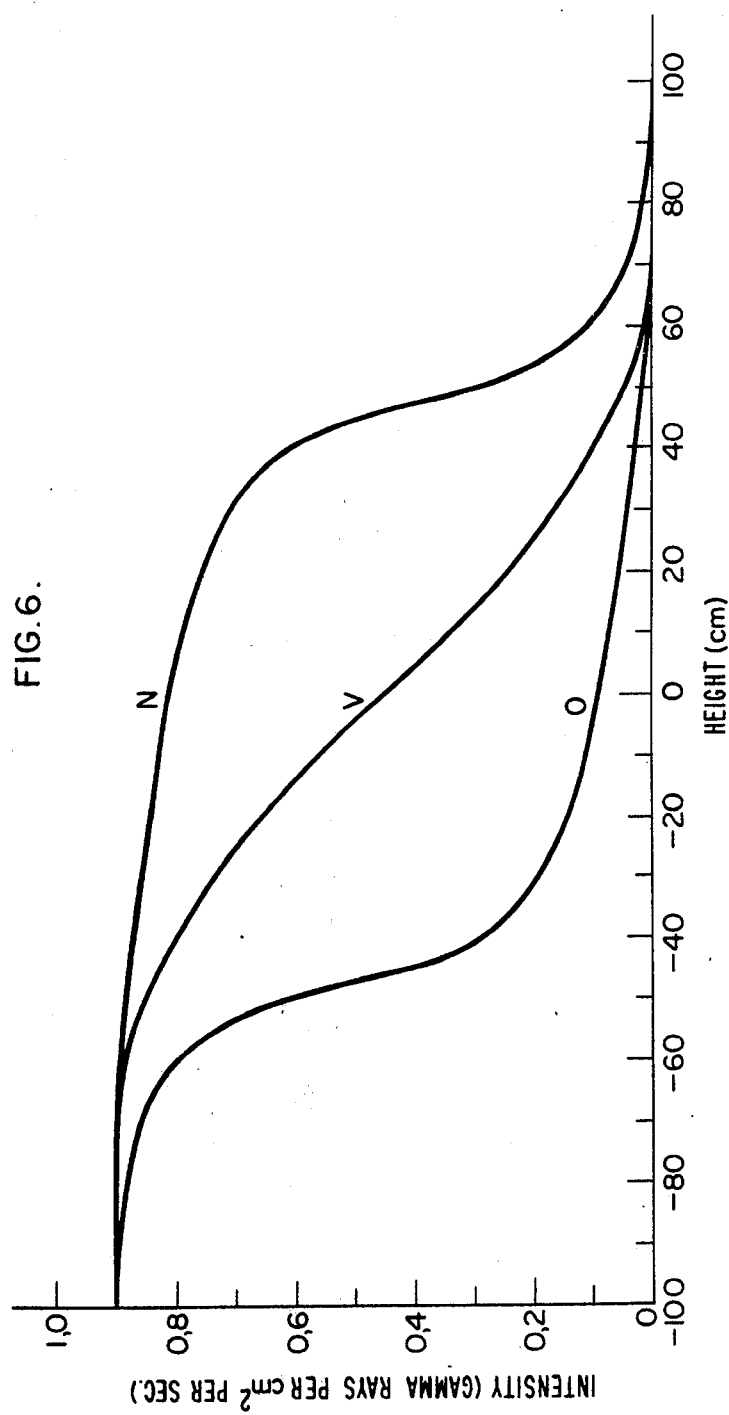
FIGS. 6–11 are graphs indicating the results of calculations made by means of a mathematical model of the preferred embodiment of the method according to the invention.
Figure 9:
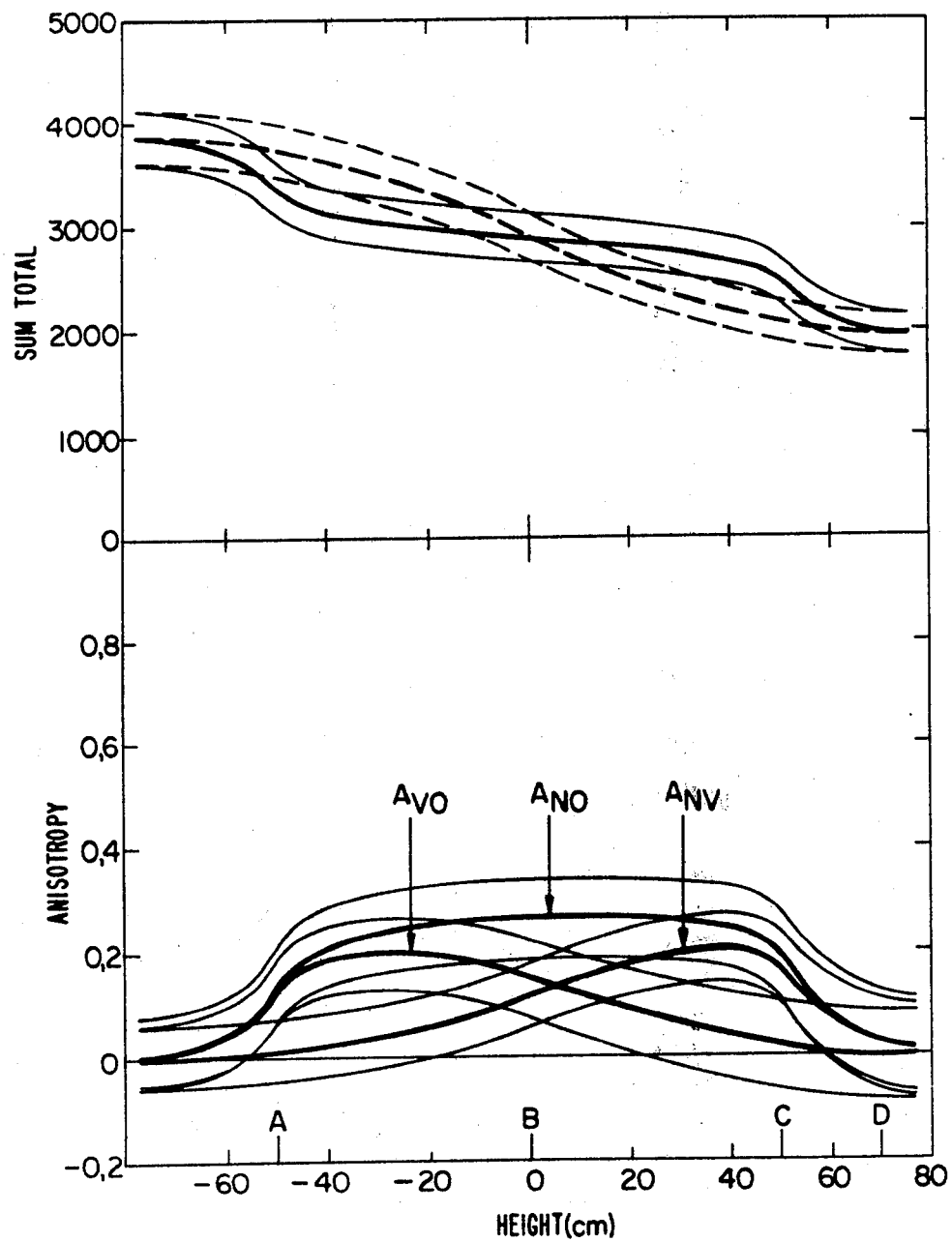
Figure 10:
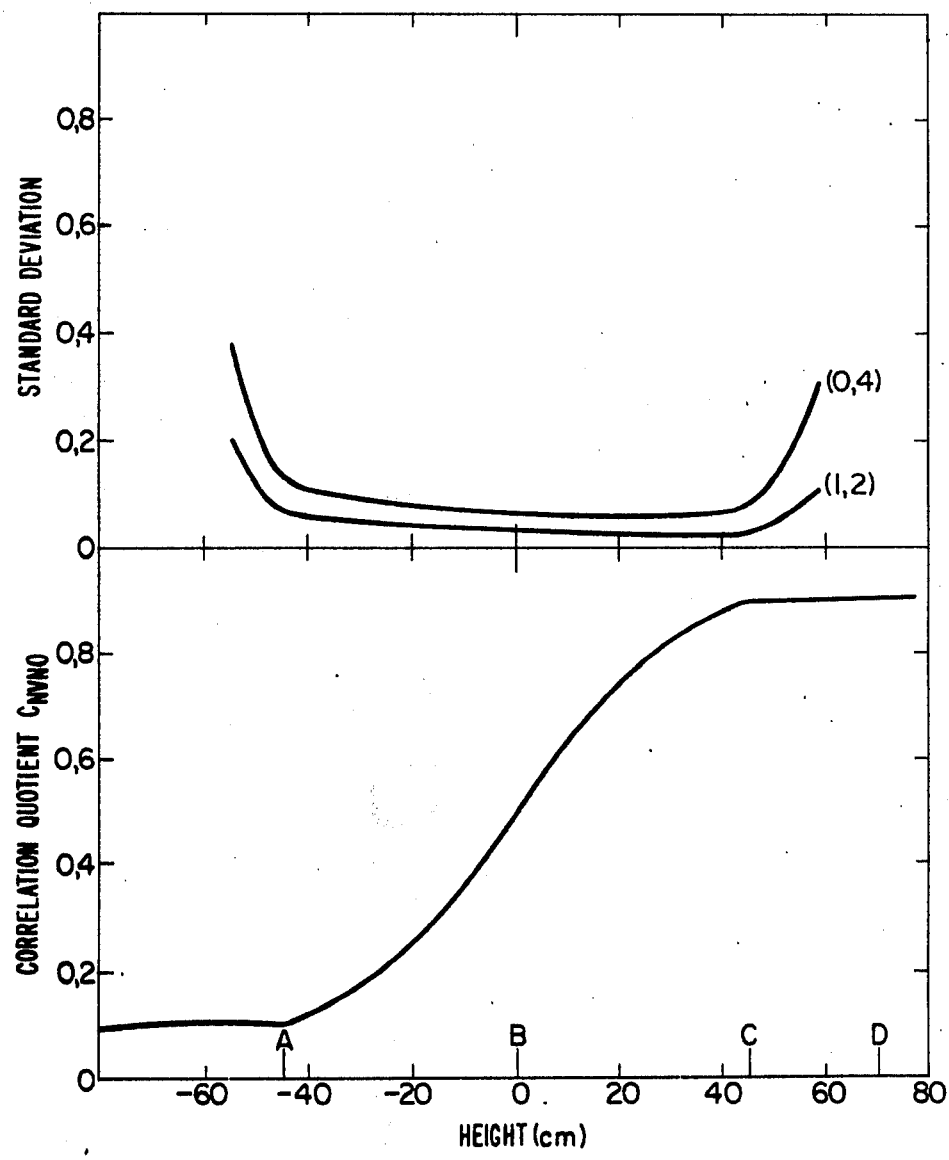
Figure 11:
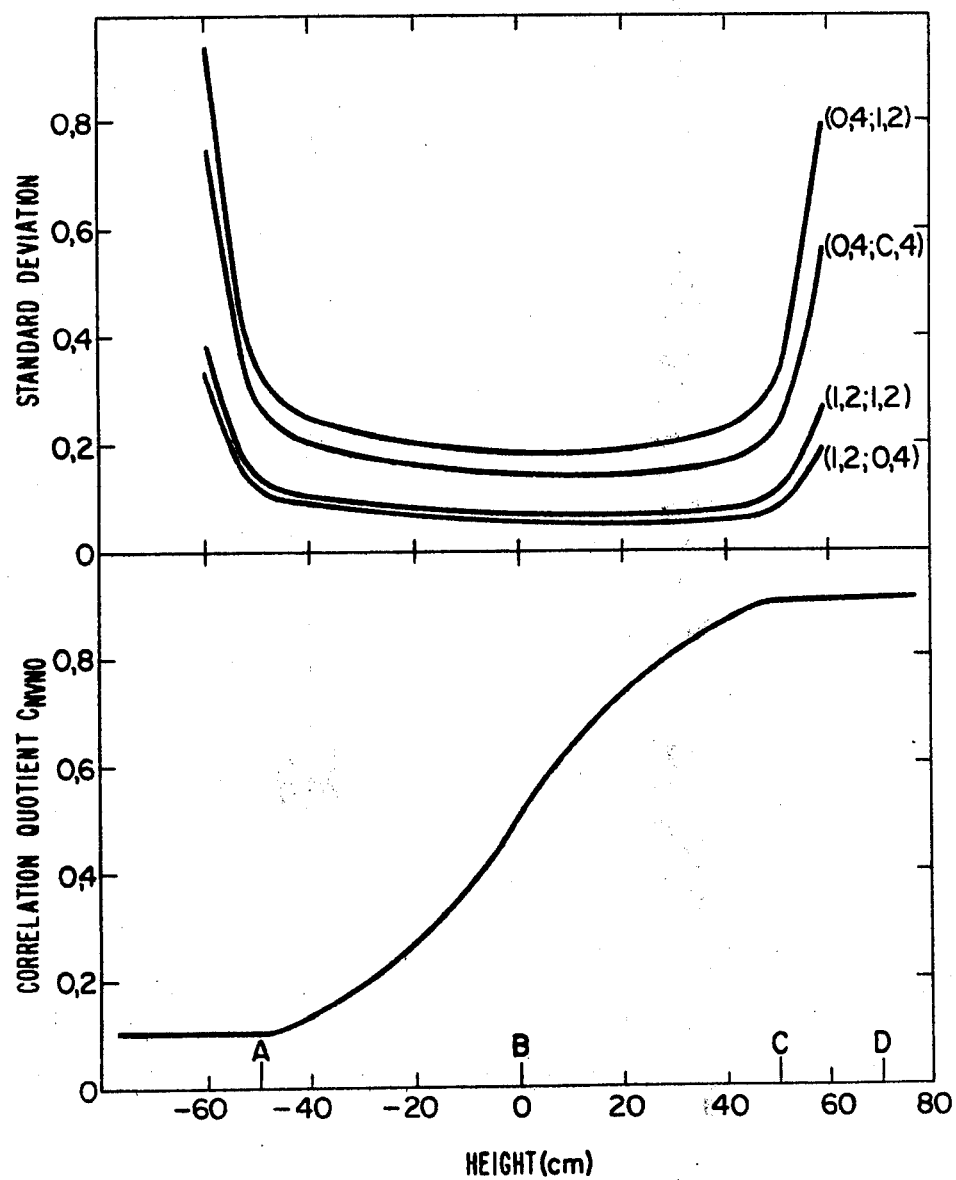

This preferred embodiment of the invention has been investigated by means of a further mathematical model in order to decide if statisically significant results may be obtained in typical cases for a given length of the pipeline. The results of these calculations are indicated in the FIGS. 6-11, of which the FIGS. 6 and 7 are graphs showing the gamma radiation intensity, FIGS. 8 and 9 indicate anisotropies and FIGS. 10 and 11 show correlation quotients.

The previously mentioned cylindric model used for the purpose of calculating the radiation intensity within a measuring device disposed in a pipeline, is for the present object modified in such a way that the intensity may be calculated at an arbitrary level with respect to the ocean floor. The results of such calculations are indicated in FIG. 6 which show the gamma radiation intensity without concrete jacket, for the lower (N), upper (O) left (or right) (V) detector positions as a function of the height of the pipeline axis with respect to the ocean floor. The source strength of the sea bottom sediment was assumed to be $S_{vo} = 1.0$ gamma rays/cm³·sec.

Figure 7:
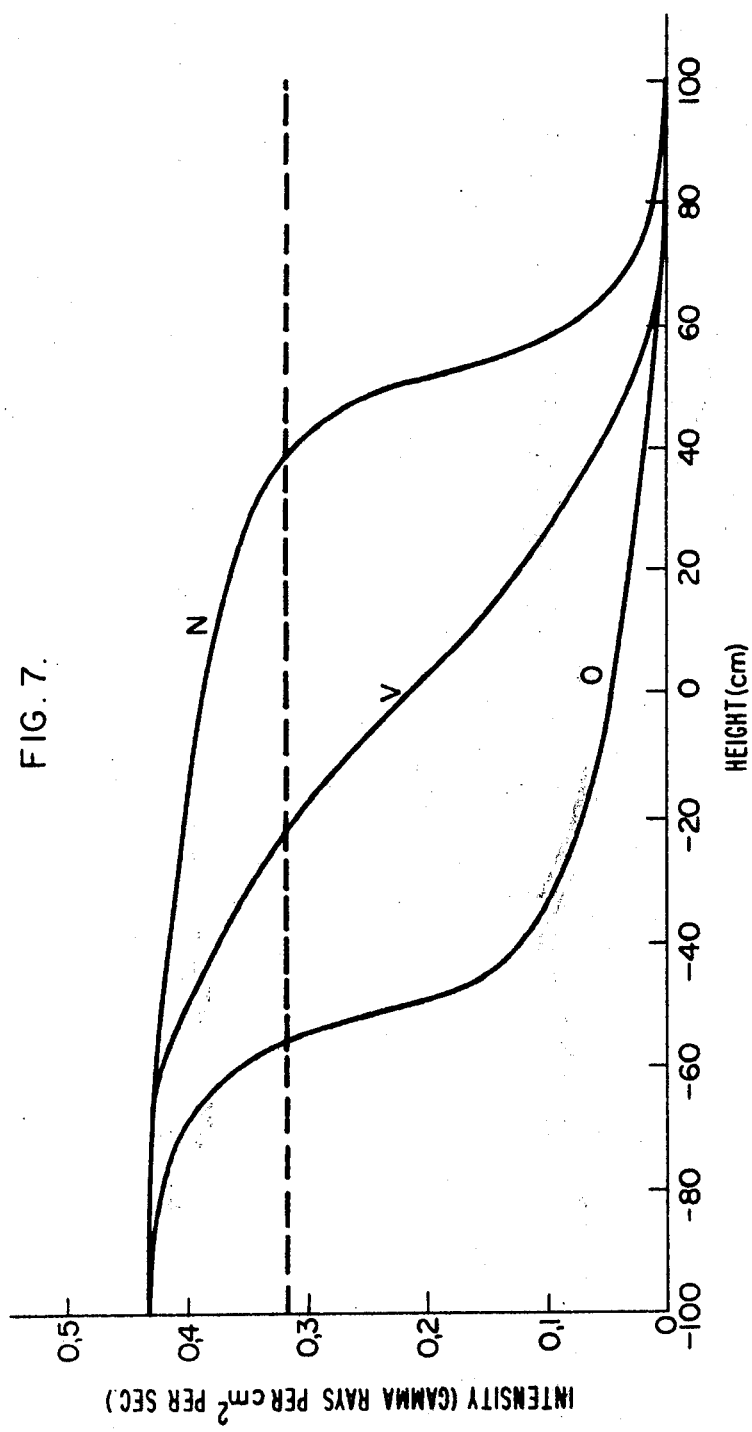

For the case the pipeline is provided with a concrete jacket, FIG. 7 shows the corresponding intensity of the gamma radiation from the sea bottom and the radiation from the concrete jacket (broken line) for the lower (N), upper (O), left (or right) (V) detector position. The source strength of both sediment and concrete jacket is $S_{vo} = S_{v1} = 1.0$ gamma rays/cm³·sec.

The support and covering of the pipeline may be expressed as anisotropies of the natural background radiation. The down/up anisotropy may be defined as:

$$A_{NO} = \frac{(N - O)}{(N + O)}$$

In the same manner the down/side anisotropy may be defined as:

$$A_{NV} = \frac{(N - \frac{1}{2}(V + H))}{(N + \frac{1}{2}(V + H))},$$

and the side/up anisotropy as:

$$A_{vo} = \frac{(\frac{1}{2}(V+H) - O)}{(\frac{1}{2}(V+H) + O)},$$

wherein N, O, V and H are the number of counts within a certain time interval for the lower, upper, left and right detector of the set, respectively.

Figure 8:
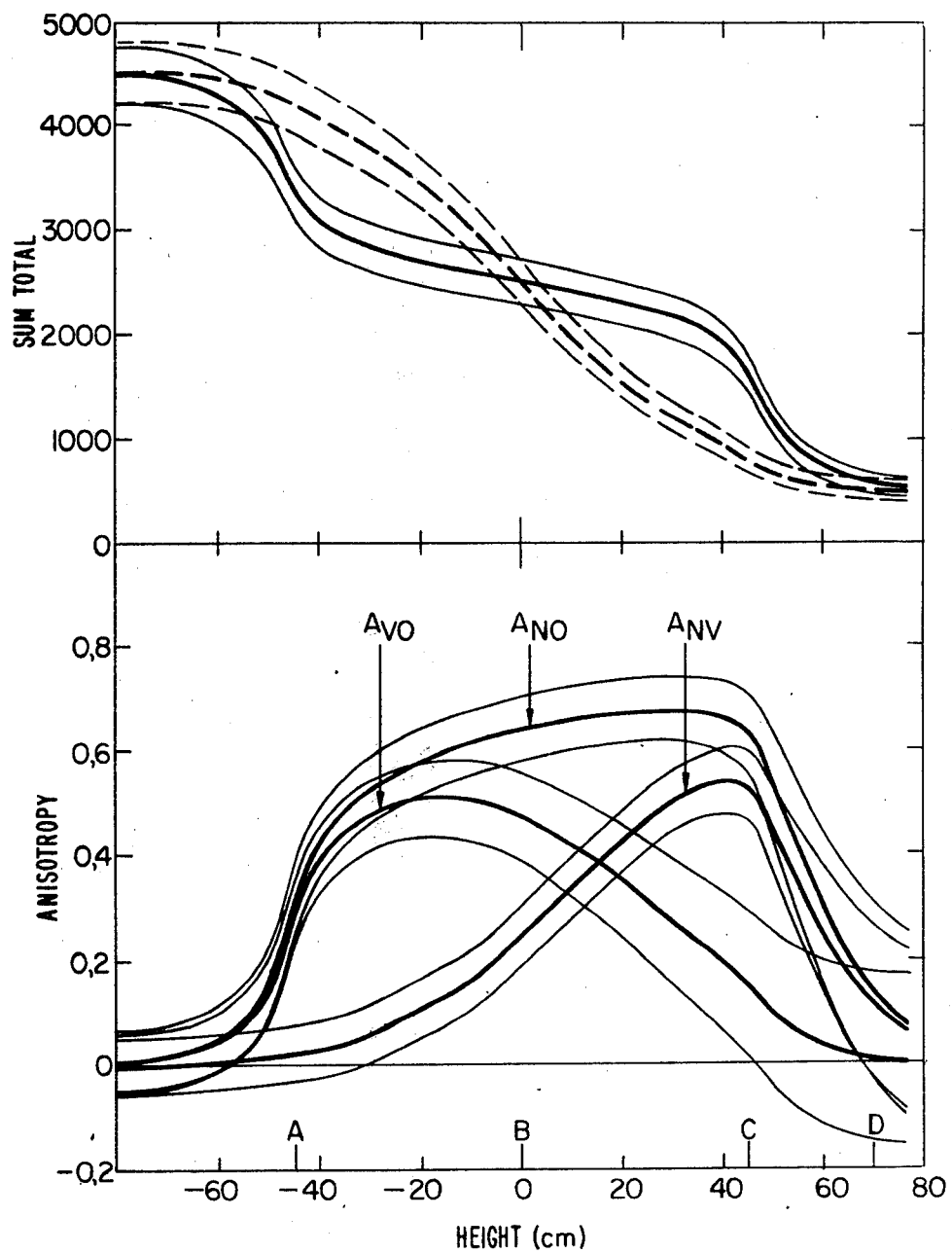

FIG. 8 (lower part) shows the counting rate anisotropies $A_{vo}$, $A_{NO}$ and $A_{NV}$ without concrete jacket. In the upper part of the Figure the sum total of the counts performed by the lower and upper detectors in the set, respectively, is shown by fully drawn graphs, whereas the sum total of the counts performed by the left and right detectors in the set, respectively, is indicated by broken graphs. The thinner lines on each side of the above graphs indicate a reliability limit of 99.74% for a counting time of 8 seconds and with a source strength of $S_{vo} = 1.2$ gamma rays/cm·sec.

FIG. 4 shows the corresponding anisotropies with a concrete jacket and source strengths of $S_{vo} = S_{v1} = 1.2$ gamma rays/cm$^3$·sec.

Alternatively, the support and covering of the pipeline may be expressed as a correlation quotient, which may be defined by the equation:

$$C_{NVNO} = \frac{(N - \frac{1}{2}(V+H))}{N - O}.$$

Whereas the anisotropies defined above are dependent of the source strengths of sediment and concrete, the above correlation quotient is, with mechanical and electronic symmetry, independent of the source strengths within statistical limits and only dependent of geometric factors.

The correlation quotient is shown as a function of the height in the lower parts of FIG. 10 (without concrete jacket) and FIG. 11 (with concrete jacket), respectively. The standard deviation is shown as a function of the height for two source strengths in the upper part of FIG. 10 and for four combinations of source strengths ($s_{vo}$:$S_{v1}$) in FIG. 11.

The anisotropies may be used to distinguish the following positions of the pipeline:

A (the pipeline barely covered in the sea bottom)
B (the pipeline axis at the level of the sea bottom)
C (the pipeline resting at the sea bottom)
D (the pipeline suspended above the sea bottom)

The correlation quotient is independent of the source strengths and approximately a linear function of the level of the pipeline axis with respect to the sea bottom within a range corresponding to the radius of the pipeline, above and below the sea bottom.

What is claimed:

1. Method for testing the support and/or covering of an oil or gas pipeline situated at the bottom of a water formation, particularly at the ocean floor,
characterized in that the natural radioactivity of the materials surrounding said pipeline is measured and compared with previously measured values of natural radioactivity of water and the supporting and/or covering materials, respectively.

2. Method as claimed in claim 1,
characterized in that the natural radioactivity is measured by means of a measuring device which is conveyed through the pipeline and comprises at least one radiation detector.

3. Method as claimed in claim 2,
characterized in that said measuring device is conveyed through the pipeline by the oil or gas flow in the same.

4. Method as claimed in claim 2,
characterized in that said measuring device records the values measured by the radiation detector.

5. Method as claimed in claim 2,
characterized in that the measuring device records the counts produced by a joint counter, which counts every pipe joint passed by the device in order to register the distance passed along the pipeline.

6. Method as claimed in claim 4,
characterized in that the measuring device, after its passage through the pipeline, is removed from the same and the recorded values collected before further use of the device.

7. Method as claimed in claim 2,
characterized in that at least one set of four radiation detectors, having approximately the same counting efficiency, is symmetrically disposed with respect to the axis of the pipeline, the counts of each radiation detector being compared with the counts of the other detectors in the set.

8. Measuring device for testing the support and/or covering of an oil or gas pipeline situated at the bottom of a water formation, particularly at the ocean floor, comprising at least one instrument casing for measuring and comparing the natural radioactivity of materials surrounding the pipeline with previously measured values of material radioactivity of water and the supporting and/or covering materials, respectively, the device further comprising a casing carrier, said instrument casing being detachably connected to said carrier.

9. Measuring device as claimed in claim 8,
characterized in that said casing carrier is provided with a drive sleeve.

10. Measuring device as claimed in claim 8 adapted for conveyance through the pipeline, characterized in that the casing carrier is provided with wheels disposed to run along the inside of the pipeline wall during said conveyance of the measuring device.

11. Measuring device as claimed in claim 10,
characterized in that said wheels are peripherally disposed around the device in a manner to effect a centering of the measuring device in the pipeline.

12. Measuring device as claimed in claim 10,
characterized in that said wheels are connected with the casing carrier by means of spring biased arms disposed to urge the wheels against the pipeline wall.

13. Measuring device as claimed in claim 8,
characterized in that said instrument casing is provided with a radiation detector disposed to feed an electronic memory for storing the measured values.

14. Measuring the device as claimed in claim 13,
characterized in that said radiation detector is a plastic scintillator.

15. Measuring device as claimed in claim 13,
characterized in that said radiation detector is a NaI(Tl) crystal.

16. Measuring device as claimed in claim 8,
characterized in that it comprises at least one set of four peripherally disposed radiation detectors which are symmetrically arranged with respect to the horizontal and vertical planes, respectively, through the pipeline axis.

17. Measuring device as claimed in claim 16, characterized in that the axis of the device is approximately coincident with the pipeline axis.

18. Measuring device as claimed in claim 16, characterized in that it is approximately symmetrically shaped with respect to the horizontal and vertical planes, respectively, through the axis of the device.

19. Measuring device as claimed in claim 16, characterized in that it is provided with a load suspended below the centre of gravity of the device.

* * * * *